(12) United States Patent
Miller et al.

(10) Patent No.: US 8,715,717 B2
(45) Date of Patent: May 6, 2014

(54) COMPOSITION FOR ANIMAL CONSUMPTION

(75) Inventors: Cheryl C. Miller, Lawrence, KS (US); Dennis Jewell, Lawrence, KS (US); William D. Schoenherr, Hoyt, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 1728 days.

(21) Appl. No.: 10/933,749

(22) Filed: Sep. 3, 2004

(65) Prior Publication Data

US 2005/0100584 A1 May 12, 2005

Related U.S. Application Data

(60) Provisional application No. 60/608,935, filed on Sep. 5, 2003.

(51) Int. Cl.
*A23K 1/17* (2006.01)
*A23K 1/165* (2006.01)

(52) U.S. Cl.
USPC ........................................................ 424/442

(58) Field of Classification Search
USPC ........................................................ 424/442
See application file for complete search history.

(56) References Cited

U.S. PATENT DOCUMENTS

| | | | | |
|---|---|---|---|---|
| 4,112,123 A | * | 9/1978 | Roberts | 426/72 |
| 4,401,657 A | * | 8/1983 | Kashiwabara et al. | 514/21 |
| 4,804,549 A | * | 2/1989 | Howley et al. | 426/98 |
| 5,339,771 A | | 8/1994 | Axelrod | A01K 29/00 |
| 5,419,283 A | | 5/1995 | Leo | A01K 29/00 |
| 5,422,127 A | * | 6/1995 | Dube et al. | 426/73 |
| 5,968,791 A | * | 10/1999 | Davies et al. | 435/134 |
| 6,156,355 A | * | 12/2000 | Shields et al. | 426/74 |
| 6,204,291 B1 | * | 3/2001 | Sunvold et al. | 514/556 |
| 6,254,910 B1 | * | 7/2001 | Paluch | 426/282 |

FOREIGN PATENT DOCUMENTS

| | | |
|---|---|---|
| EP | 0 519 458 A | 12/1992 |
| EP | 0519458 | 12/1992 |
| EP | 0 600 439 A | 6/1994 |
| EP | 0600439 | 6/1994 |
| JP | H01-309643 | 12/1989 |
| JP | 2-100635 A | 4/1990 |
| JP | H02-299555 | 11/1990 |
| JP | 3-198748 A | 8/1991 |
| JP | H06-62763 | 3/1994 |
| JP | 06-153812 | 6/1994 |
| JP | 2002-507401 | 3/2002 |
| JP | 2002-138297 A | 5/2002 |

(Continued)

OTHER PUBLICATIONS

Malainey et al, Journal of Archaeological Science (1999) 26, 95-103.*

(Continued)

*Primary Examiner* — Benjamin Packard
(74) *Attorney, Agent, or Firm* — Thomas M. Hunter

(57) ABSTRACT

This invention is directed generally to compositions (including foods, supplements, treats, toys, etc.) for animal consumption, particularly compositions that tend to aid in weight loss or reduction in weight gain, and particularly compositions that comprise one or more medium chain fatty acid triglycerides ("MCT"). This invention also is directed generally to methods for using such compositions. This invention is further directed generally to processes for making such compositions.

15 Claims, 2 Drawing Sheets

(56) References Cited

FOREIGN PATENT DOCUMENTS

| JP | 2002-180082 | 6/2002 |
|---|---|---|
| JP | 2002-537861 | 11/2002 |
| JP | 2003-501056 | 1/2003 |
| JP | 2005-510257 | 4/2005 |
| WO | WO 00/49891 | 8/2000 |
| WO | WO 00/74497 | 12/2000 |
| WO | WO 00/74497 A1 | 12/2000 |
| WO | WO 0072854 A1 * | 12/2000 |
| WO | WO 01/95739 | 12/2001 |
| WO | WO 01/95739 A2 | 12/2001 |
| WO | WO 02/11550 | 2/2002 |
| WO | WO 03/047363 | 6/2003 |
| WO | WO 2005/025322 | 3/2005 |

OTHER PUBLICATIONS

RedBarn Products (http://web.archive.org/web/20021210210226/www.redbarninc.com/filled_treats.html, published date Aug. 2, 2002, accessed Sep. 16, 2008).*
Rolls et al (Journal of Clinical Nutrition, 48 (1): 66. (1988).*
American Feed Control Officials, "AAFCO Dog Food Nutrient Profiles Based on Dry Matter", Official Publication, 126-140 (2003).
American Feed Control Officials, "Supplement", Official Publication, 220 (2003).
Beynen et al., "Plasma lipid concentrations, macronutrient digestibility and mineral absorption in dogs fed a dry food containing medium-chain triglycerides", *J. Anim. Phys. Anim. Nutr.*, 86:306-312 (2002).
Binnert, "Influence of human obesity on the metabolic fate of dietary long- and medium-chain triglycerols", *Am. J. Clin. Nutr.*, 67:595-601 (1998).
Cleary et al., "Genotype and diet effects in lean and obese Zucker rats fed either safflower or coconut oil diets", *Proc. Soc. Exp. Biol. Med.*, 220(3):153-161 (1999).
Lasekan et al., "Energy expenditure in rats maintained with intravenous or intragastric infusion of total parenteral nutrition solutions containing medium- or long-chain triglyceride emulsions", *J. Nutr.*, 122:1483-1492 (1992).
Nutrient Requirements of Domestic Animals, *Nutrient Requirements of Horses*, 5$^{th}$ Rev. Ed., National Academy Press, Washington, D.C. (1989).
Nutrient Requirements of Domestic Animals, *Nutrient Requirements of Poultry*, 9$^{th}$ Rev. Ed., National Academy Press, Washington, D.C. (1994).
Nutrient Requirements of Domestic Animals, *Nutrient Requirements of Swine*, 10$^{th}$ Rev. Ed., National Academy Press, Washington, D.C. (1998).
Papamandjaris et al., "Medium Chain Fatty Acid Metabolism and Energy Expenditure: Obesity Treatment Implications", *Life Sciences* 62:1203-1215 (1998).
Portillo et al., "Energy Restriction with High-Fat Diet Enriched with Coconut Oil Gives Higher UCP1 and Lower White Fat in Rats", *Int'l J. Obesity Rel. Metab. Disord.*, 22:974-979 (1998).
Rothwell et al., "Stimulation of Thermogenesis and Brown Fat Activity in Rats Fed Medium Chain Triglyceride", *Metabolism*, 36:128-130 (1987).
St-Onge et al., "Physiological Effects of Medium-Chain Triglycerides: Potential Agents in the Prevention of Obesity", *P.J. Nutr.*, 132:329-332 (2002).

Tsuji et al., "Dietary Medium-Chain Triacylglycerols Supress Accumulation of Body Fat in a Double-Blind, Controlled Trial in Healthy Men and Women", *J. Nutr.*, 131:2853-2859 (2001).
Traul et al., "Review of the toxicologic properties of medium-chain triglycerides", *Food Chem. Toxicol.*, 38(1):79-98 (2000).
Van Dongen et al., "An Observation: The High Intade of Medium-Chain Triglycerides Elevates Plasma Cholesterol in Dogs", *Folia Vet.*, 44:173 (2000).
Van Wymelbeke et al., "Substrate oxidation and control of food intake in men after a fat-substitute meal compared with meals supplemented with an isoenergetic load of carbohydrate, long-chain triacylglycerols, or medium-chain triacylclycerols", *Am. J. Clin. Nutr.*, 74:620-630 (2001).
White et al., "Enhanced postprandial energy expenditure with medium-chain fatty acid feeding is attenuated after 14 d in premenopausal women," *Am. J. Clin. Nutr.*, 69:883-889 (1999).
Hand, M. S., et al., "Gastrointestinal and Exocrine Pancreatic Disease", Small Anim. Clin Nutr, 4$^{th}$ ed., p. 769, Walsworth Publishing Com, Marceline, MO (2000).
Hill, C., Clin Care Nutr in the Watham Book of Clin Nutr of the Dog and Cat, pp. 7-45, Elsevier Sce Ltd., Oxford (1994).
Database WPI, Section Ch, Week 200152, Derwent Publications Ltd., AN 1994-220395, XP002312965 & JP 03 203441 (Miyoshi Yushi KK), Aug. 27, 2001 (Abstract).
Database WPI, Section Ch, Week 199228, Derwent Publications Ltd., AN 1992-232145, XP002312966 & NL 9 101 992 (KAO Corp), Jun. 16, 1992 (Abstract).
International Search Report for International Application No. PCT/US04/28762 mailed on Apr. 12, 2005.
Standard Tables of Food Compositions in Japan 1987 ed, published by Japan Livestock Industry Associateion, pp. 108, 110, 114, 118, 120.
Miromoto, Hiroshi, Handbook of Feeds, published by Japan Scientific Feeds Association, Nov. 21, 1986, p. 162.
Fatty Ester Products of Kao Corporation, Nov. 22, 2009.
Food Additive Products of Kao Corporation, Nov. 22, 2009, p. 3.
Chiang et al., "Effects of medium chain triglyceride on energy metabolism, growth and body fat in broilers," Journal of the Chinese Society of Animal Science, vol. 19, No. 1/2, pp. 11-19, 1990, XP002312964.
Standard Tables of Food Composition in Japan, 1987, Japan Livestock Industry Association, First ed., p. 74.
Yamashita et al., "Digestive Absorption and Metabolism of Fat and Oil, Especially Medium Chain Triglyceride," New Food Industry, Shokuhin Shizai Kenkyukai, Co., 1982, 24(4):28-33.
Database WPI, Section Ch, Week 200152, Derwent Publications Ltd., London, GB, Miyoshi Yushi, KK, JP 03 203441 B2, (Aug. 27, 2001).
Database WIP, Section Ch, Week 199228, Derwent Publications Ltd., London, GB, KAO Corp., NL 9 101 992 A (Jun. 16, 1992).
Database FSTA 'Online!, International Food Information Service (IFIS), Frankfurt-Main, DE, et al, "Effects of medium triglyceride on energy metabolism, growth and body fat in broilers," J. of the Chinese Soc. of Animal Science, 19:1/2 (1990).
St-Onge, et al., "Physiological Effects of Medium-Chain Triglycerides: Potential Agents in the Prevention of Obesity," Recent Advances of Nutri. Sciences, 132:12, 329-332 (2002).

* cited by examiner

COMPOSITION FOR ANIMAL CONSUMPTION

PRIORITY CLAIM TO RELATED PATENT APPLICATION

This patent claims priority to U.S. Provisional Application No. 60/608,935 (filed Sep. 5, 2003). The entire text of the above-referenced patent application is incorporated by reference into this patent.

FIELD OF THE INVENTION

This invention is directed generally to compositions (including foods, supplements, treats, toys, etc.) for animal consumption, particularly compositions that tend to aid in weight loss or reducing weight gain, and particularly compositions that comprise one or more medium chain fatty acid triglycerides ("MCT"). This invention also is directed generally to methods for using such compositions. This invention is further directed generally to processes for making such compositions.

BACKGROUND OF THE INVENTION

Medium chain triglycerides (MCT) are a family of triglycerides generally containing saturated fatty acid chains of from about 8 to about 12 carbon atoms. These fatty acid chains are often predominantly caprylic acid (8-carbon) and capric acid (10-carbon) chains, with lesser amounts of caproic acid (6-carbon) and lauric acid (12-carbon) chains.

MCT have reportedly been used for parenteral nutrition in humans requiring supplemental nutrition, and are reportedly also increasingly being used in foods, drugs, and cosmetics. MCT have additionally reportedly been found to be non-toxic in acute toxicity tests for a range of animal species.

In contrast to MCT, long chain triglycerides (LCT) contain saturated and unsaturated fatty acid residues with greater than 12 carbons. Differences in fatty acid chain length and degree of saturation reportedly have been observed to lead to differences in digestion, absorption, and transport in at least some species. Specifically, for example, medium chain fatty acids (MCFAs) reportedly have been observed to have a greater tendency to enter portal blood directly and be transported to the liver for rapid oxidation, whereas long chain fatty acids (LCFAS) reportedly have been observed to have a greater tendency to be packaged into chylomicrons and transported into the lymphatic system, allowing for extensive uptake into the adipose tissue in at least some animals. MCFAs also reportedly have been observed to have a tendency to enter mitochondria independent of the carnitine transport system and undergo preferential oxidation in at least some animals. Papamandjaris, et al., "Medium Chain Fatty Acid Metabolism and Energy Expenditure: Obesity Treatment Implications", Life Sciences, 62:1203-1215 (1998). It has been hypothesized that relatively rapid metabolism of MCT may, relative to LCT, increase energy expenditure, decrease deposition of MCT into adipose tissue, and result in faster satiety in at least some species. See St-Onge, M., et al., "Physiological Effects of Medium-Chain Triglycerides: Potential Agents in the Prevention of Obesity", P. J. Nutr., 132:329-332 (2002). See also, Rothwell, N., et al., Metabolism, 36:128-130, 1987 (reporting that feeding MCT to humans increases energy expenditure and fat oxidation, and discussing potential for use of MCT in weight management regimes). See also, Tsuji, H., et al., "Dietary Medium-Chain Triacylglycerols Suppress Accumulation of Body Fat in a Double-Blind, Controlled Trial in Healthy Men and Women", Nutr., 131: 2853-2859 (2001) (discussing reduction of body weight and fat using MCT diet in humans). See also, Portillo, M., et al., "Energy Restriction with High-Fat Diet Enriched with Coconut Oil Gives Higher UCP1 and Lower White Fat in Rats", Int'l J. Obes. Relat. Metab. Disord., 22: 974-979 (1998) (reporting that MCT-enriched diet is effective in stimulating uncoupling protein-1 (UCP1) expression during ad libitum feeding and preventing UCP1 down regulation during food restriction in rats). See also, Lasekan, J., et al., "Energy expenditure in rats maintained with intravenous or intragastric infusion of total parenteral nutrition solutions containing medium- or long-chain triglyceride emulsions", J. Nutr., 122: pps. 1483-1492 (1992) (reporting lower weight gain and greater energy expenditure in rats having MCT-supplemented parenteral nutrition relative to rats having LCT-supplemented parenteral nutrition).

Despite the reported advantages of MCT, there have been difficulties in developing MCT-containing foods. Some studies, for example, have reported that MCT-containing foods tend to have poor palatability.

Thus, there continues to be a need for compositions for animal consumption, particularly those that aid in weight loss or reduction in the rate of weight gain.

SUMMARY OF THE INVENTION

This invention is directed to compositions for animal consumption, particularly compositions that tend to aid in weight loss or reduce the rate of weight gain. It is contemplated that such compositions are suitable to be used with mammals, including non-human mammals such as non-human primates (e.g., monkeys, chimpanzees, etc.), companion animals (e.g., dogs, cats, horses, etc.), farm animals (e.g., goats, sheep, pigs, cattle, etc.), laboratory animals (e.g., mice, rats, etc.), and wild and zoo animals (e.g., wolves, bears, deer, etc.). It also is contemplated that such compositions are suitable to be used with non-mammalian animals, such as companion, farm, zoo, and wild birds (e.g., including, for example, song birds, parrots, ducks, geese, chickens, turkeys, ostriches, etc.).

Briefly, therefore, this invention is directed, in part, to a composition for animal consumption, such as, for example, a food, nutritional supplement, treat, or toy. The composition comprises from about 2% to about 25% (based on dry weight of the composition) of one or more medium chain fatty acid triglycerides (i.e., triglycerides containing saturated fatty acid chains comprising from about 8 to about 12 carbons).

This invention also is directed to a treat, wherein the treat comprises one or more medium chain fatty acid triglycerides.

This invention also is directed to a toy, wherein the toy comprises one or more medium chain fatty acid triglycerides.

This invention also is directed to processes for preparing such compositions, treats, and toys.

This invention also is directed to methods for using such compositions, treats, and toys to aid in weight loss or reducing weight gain.

DETAILED DESCRIPTION OF THE PREFERRED EMBODIMENTS

Figure 1:
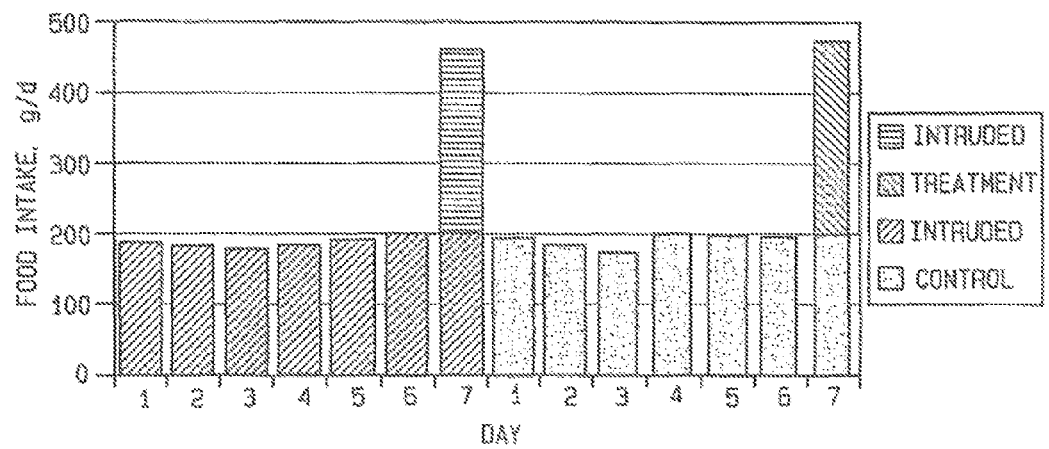
FIG. 1 compares observed food intake over two weeks with dogs fed MCT-supplemented food and food not supplemented with MCT.

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

In accordance with this invention, we have found that inclusion of MCT into an animal's diet (preferably into the animal's food) as described in this patent tends to increase satiety and the rate at which the animal will lose weight (or decrease the rate at which an animal will gain weight). We have found, for example, that such inclusion of MCT in pet food enhances the rate of weight loss relative to a food without MCT, even when similar amounts (calories) are consumed. This invention generally allows feeding of an advantageous concentration of MCT without negative effects on food intake or the health of the animal.

As used in this patent, a "triglyceride" is an ester of three fatty acids and glycerol. Triglycerides have the general chemical formula, $CH_2(OOCR^1)CH(OOCR^2)CH_2(OOCR^3)$, and correspond in structure to the following Formula I:

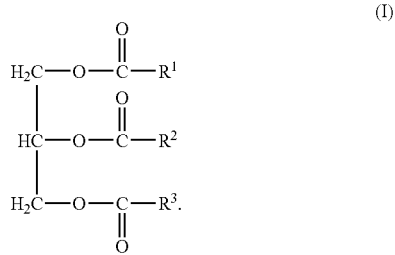

Each of $OOCR^1$, $OOCR^2$, and $OOCR^3$ is a fatty acid residue. Each such residue is independently selected, i.e., $R^1$, $R^2$, and $R^3$ can be identical or different.

As used in this patent, "MCT" is one or more triglycerides containing saturated fatty acid chains of from about 8 to about 12 carbons. Each fatty acid chain in the triglyceride may be identical or different. Sources for MCT include, for example, coconut oil, macadamia oil, palm oil, palm kernel oil, and mixtures of such oils.

The MCT may be included in various types compositions, such as, for example, a food, supplement, treat, or toy (typically a chewable and consumable toy). The MCT is preferably present in the composition in an amount that is from about 2% to about 25% (or from about 5% to about 20%, or from about 7% to about 18%, or from about 12% to about 16%) based on the dry weight of the composition. It is contemplated that use of such proportions of MCT in accordance with this invention will increase an animal's energy expenditure even in the absence of any change in caloric intake, assist in weight loss through modification of energy use without changing preference for the composition, and/or beneficially change metabolism without decreasing taste.

In some embodiments, the MCT-containing composition is a food. Although both liquid and solid foods are contemplated, solid foods are typically preferred. Where the food is solid, the MCT may be coated on the food, incorporated into the food, or both. Contemplated foods include both dry foods or wet foods. The non-MCT components of the food and their preferred proportions include those listed in Table 1.

TABLE 1

| Component | Preferred proportion of the composition (% of dry weight of composition) |
|---|---|
| Carbohydrate (preferably a nitrogen-free or essentially nitrogen-free extract) | from about 0% to about 50%, or from about 5% to about 45% |
| Protein | from about 5% to about 70%, or from about 10% to about 70%, or from about 10% to about 60% |
| Fat | from about 2% to about 50%, or from about 5% to about 50%, or from about 5% to about 40% |
| Dietary fiber | from about 0% to about 40%, or from about 1% to about 20%, or from about 1% to about 5.5% |
| Nutritional balancing agents (e.g., vitamins and minerals) | from about 0% to about 15%, or from about 2% to about 8% |

In a contemplated embodiment, the composition is a food that comprises the following:
 (a) from about 2% to about 25% (or from about 5% to about 20%, or from about 7% to about 18%, or from about 12% to about 16%) MCT; and
 (b) at least one of the following:
  (i) from about 5% to about 70% (or from about 10% to about 70%, or from about 10% to about 60%) protein, and
  (ii) from about 2% to about 50% (or from about 5% to about 50%, or from about 5% to about 40%) fat.
In such an embodiment, it is contemplated that the composition also may, for example, comprise at least one of the following:
 (a) no greater than about 50% (or from about 5% to about 45%) carbohydrate,
 (b) no greater than about 40% (or from about 1% to about 20%, or from about 1% to about 5.5%) dietary fiber, and
 (c) no greater than about 15% (or from about 2% to about 8%) of one or more nutritional balancing agents.

In another contemplated embodiment, the composition is a food that comprises the following:
 (a) from about 2% to about 25% (or from about 5% to about 20%, or from about 7% to about 18%, or from about 12% to about 16%) MCT, and
 (b) from about 5% to about 70% (or from about 10% to about 70%, or from about 10% to about 60%) protein.

In another contemplated embodiment, the composition is a food that comprises the following:
 (a) from about 2% to about 25% (or from about 5% to about 20%, or from about 7% to about 18%, or from about 12% to about 16%) MCT, and
 (b) from about 2% to about 50% (or from about 5% to about 50%, or from about 5% to about 40%) fat.

In another contemplated embodiment, the composition is a food that comprises the following:
 (a) from about 2% to about 25% (or from about 5% to about 20%, or from about 7% to about 18%, or from about 12% to about 16%) MCT, (b) from about 5% to about 70% (or from about 10% to about 70%, or from about 10% to about 60%) protein, and (c) from about 2% to about 50% (or from about 5% to about 50%, or from about 5% to about 40%) fat.

In another contemplated embodiment, the composition is a food that comprises the following:

(a) from about 2% to about 25% (or from about 5% to about 20%, or from about 7% to about 18%, or from about 12% to about 16%) MCT, (b) from about 5% to about 70% (or from about 10% to about 70%, or from about 10% to about 60%) protein, (c) from about 2% to about 50% (or from about 5% to about 50%, or from about 5% to about 40%) fat, (d) no greater than about 50% (or from about 5% to about 45%) carbohydrate, (e) no greater than about 40% (or from about 1% to about 20%, or from about 1% to about 5.5%) dietary fiber, and (f) no greater than about 15% (or from about 2% to about 8%) of one or more nutritional balancing agents.

Specific preferred amounts for each component in a composition will depend on a variety of factors including, for example, the species of animal consuming the composition; the particular components included in the composition; the age, weight, general health, sex, and diet of the animal; the animal's consumption rate; the type of composition condition(s) being treated; and the like. Thus, the component amounts may vary widely, and may even deviate from the preferred proportions set forth in this patent.

The fat and carbohydrate in the compositions of the present invention may be supplied by a variety of sources, including, for example, meat, meat by-products, other animal or plant protein sources, grains, and mixtures thereof. Meat includes, for example, the flesh of poultry; fish; and mammals (e.g. cattle, swine, sheep, goats, and the like). Meat by-products include, for example, lungs, kidneys, brain, livers, and stomachs and intestines freed of their contents. Grains include, for example, wheat, corn, barley, and rice.

Fiber in the compositions of the present invention may be supplied from a variety of sources, including, for example, vegetable fiber sources such as cellulose, beet pulp, peanut hulls, and soy fiber.

Particularly in instances when the composition is an animal's food, vitamins and minerals should be included in amounts required to avoid deficiency and maintain health. These amounts are readily available in the art. The National Research Council (NRC), for example, provides recommended amounts of such ingredients for farm animals. See, e.g., *Nutrient Requirements of Swine* (10th Rev. Ed., Nat'l Academy Press, Wash. D.C., 1998), *Nutrient Requirements of Poultry* (9th Rev. Ed., Nat'l Academy Press, Wash. D.C., 1994), *Nutrient Requirements of Horses* (Fifth Rev. Ed., Nat'l Academy Press, Wash. D.C., 1989), etc. And the American Feed Control Officials (AAFCO), for example, provides recommended amounts of such ingredients for dogs and cats. See American Feed Control Officials, Incorp., Official publication, pp. 126-140 (2003).

The compositions of the present invention may further contain additives known in the art. Preferably, such additives are present in amounts that do not impair the purpose and effect provided by the invention. Examples of contemplated additives include, for example, substances that are functionally beneficial to weight management, substances with a stabilizing effect, processing aids, substances that enhances palatability, coloring substances, and substances that provide nutritional benefits.

Contemplated substances that may provide a benefit for weight management include, for example, nonfermentable fiber, carnitine, chrominium-picolinate, and the like.

Contemplated stabilizing substances include, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

Contemplated additives for coloring, palatability, and nutritional purposes include, for example, colorants; iron oxide, sodium chloride, potassium citrate, potassium chloride, and other edible salts; vitamins; minerals; and flavoring. The amount of such additives in a composition typically is up to 5% (dry basis of the composition).

Supplements include, for example, a feed used with another feed to improve the nutritive balance or performance of the total. Contemplated supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Incorp. Official Publication, p. 220 (2003). Supplements may be in various forms including, for example, powders, liquids, syrups, pills, etc.

Treats include, for example, compositions that are given to an animal to entice the animal to eat during a non-meal time. Contemplated treats for canines include, for example, dog bones. Treats may be nutritional, wherein the composition comprises one or more nutrients, and may, for example, have a composition as described above for food. Non-nutritional treats encompass any other treats that are non-toxic. The MCT can be coated onto the treat, incorporated into the treat, or both.

Toys include, for example, chewable toys. Contemplated toys for dogs include, for example, artificial bones. The MCT can form a coating on the surface of the toy or on the surface of a component of the toy, be incorporated partially or fully throughout the toy, or both. In a contemplated embodiment, the MCT is orally accessible by the intended user. There a wide range of suitable toys currently marketed. See, e.g., U.S. Pat. No. 5,339,771. See also, e.g., U.S. Pat. No. 5,419,283. It should be recognized that this invention contemplates both partially consumable toys (e.g., toys comprising plastic components) and fully consumable toys (e.g., rawhides and various artificial bones). It should be further recognized that this invention contemplates toys for both human and non-human use, particularly for companion, farm, and zoo animal use, and particularly for dog, cat, or bird use.

In preparing a composition of the present invention, the components of the composition are adjusted so that the MCT is present in the composition at a concentration of from about 2% up to 25% (or from about 5% to about 20%, or from about 7% to about 18%, or from about 12% to about 16%) based on the dry content of the composition. The MCT may, for example, be incorporated into the composition during the processing of the formulation, such as during and/or after mixing of other components of the composition. Distribution of these components into the composition can be accomplished by conventional means.

Compositions of the present invention (particularly foods) can be prepared in a canned or wet form using conventional pet food processes. In one contemplated embodiment, ground animal and poultry proteinaceous tissues is mixed with the other ingredients, including fish oils, cereal grains, other nutritionally balancing ingredients, special purpose additives (e.g., vitamin and mineral mixtures, inorganic salts, cellulose and beet pulp, bulking agents, and the like); and water sufficient for processing is also added. These ingredients preferably are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. to about 212° F. Temperatures outside this range are acceptable, but may be commercially impractical without the use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. for an appropriate time, which is dependent on, for example, the temperature used and the composition.

Compositions of the present invention (particularly foods) can be prepared in a dry form using conventional processes. In one contemplated embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix (which, in a contemplated embodiment, comprises at least 2% of the desired MCT amount for the final product). The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils (e.g., MCT), powders, and the like. Kibble also can be made from the dough using a baking process, rather than extrusion, wherein the dough is placed into a mold before dry-heat processing.

Treats of the present invention can be prepared by, for example, an extrusion or baking process similar to those described above for dry food. Other processes also may be used to either coat MCT oil on the exterior of existing treat forms, or inject it into an existing treat form.

Animal toys of the present invention are typically prepared by coating any existing toy with MCT.

EXAMPLES

The following examples are merely illustrative, and not limiting to this disclosure in any way.

Example 1

Balanced, dry pet foods were formulated that contained various amounts of coconut oil (12 and 5% as mixed—see below). The coconut oil was incorporated into the foods by injecting 2% into the preconditioner before kibble extrusion, and coating the remaining amount on hot kibbles. The kibbles were then allowed to cool. All foods were stored at room temperature before use. The foods had the compositions shown in Table 2 below.

TABLE 2

Food Compositions for Animal Studies

| | Study | | | | |
|---|---|---|---|---|---|
| | 1 & 2 | 3 | 3 | 4 | 4 |
| Coconut Oil (%) | 14.2 | 7.1 | 14.2 | 13.0 | 13.0 |
| Protein (%) | 19.7 | 24.7 | 24.7 | 24.8 | 24.8 |
| Fat (%) | 20.6 | 16.9 | 16.9 | 22.0 | 22.0 |
| Carbohydrate (%) | 53.8 | 51.0 | 51.0 | 46.3 | 27.6 |
| Crude Fiber (%) | 0.37 | 2.6 | 2.6 | 1.4 | 21.0 |

The protein, fat, carbohydrate, and crude fiber components were nutrients to balance the formula to meet nutritional needs. All control formulations were designed to be nutrient-matched.

A. Study 1

Study 1 utilized a 2-week crossover design with an intruded meal at the end of each week. The dogs were fed slightly below maintenance requirements (requirement=(1.4)(BW$^{0.75}$)(70)). The foods consisted of a dry dog food containing MCT in the form of coconut oil (14.2% of diet), and a control food containing an equal amount of fat (LCT) from other sources. The dogs fed coconut oil lost more weight than control fed dogs, as shown in Table 3 below:

TABLE 3

Average Body Weights (grams) in Study 1

| Treatment | Day Zero | Day 7 | Difference |
|---|---|---|---|
| Combined control | 16.31 | 16.05 | −0.26 |
| Combined test | 16.39 | 15.98 | −0.41 |

Food consumption was equal between the two treatment groups (see FIG. 1). This is unexpected in view of other companion animal studies reporting MCT-containing foods as having poor palatability that leads to insufficient food intake. See, e.g., Van Dongen, A. M., et al., *Folia Vet.*, 44:173 (2000). See also, e.g., Hand, M. S., et al, *Small Anim Clin Nutr*, p. 769 (4th ed., Walsworth Publishing Co., Marceline, MO (2000)). See also, e.g., Hill, C., "Clin Care Nutr", *The Waltham Book of Clin Nutr of the Dog and Cat*, pps. 7-45 (Elsevier Sce Ltd., Oxford (1994)). Because intake was equal with the control, inclusion of the 14.2% coconut oil increased the amount of body weight loss over a week without changing the amount of calories consumed.

B. Study 2

Figure 2:
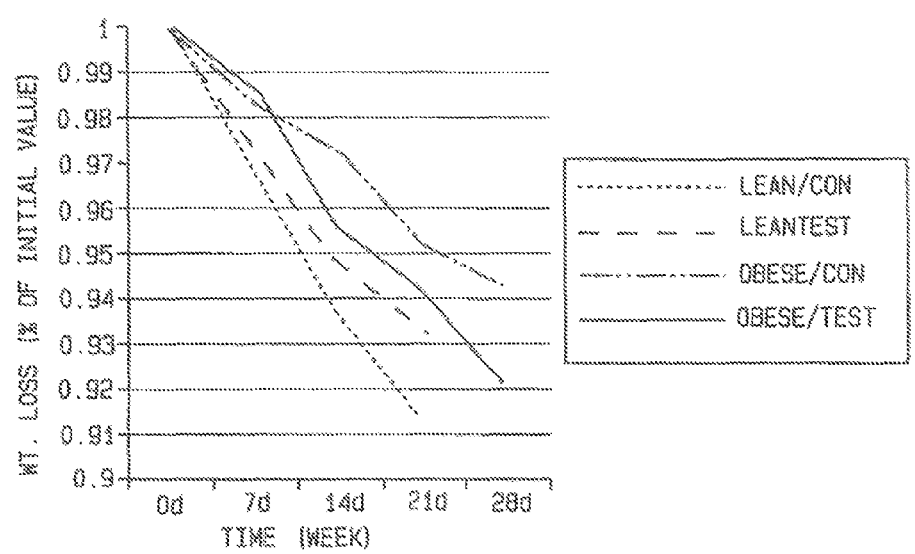
FIG. 2 compares observed body weight changes in lean-prone and obese-prone dogs fed MCT-supplemented rations and rations not supplemented with MCT.

Study 2 utilized a lean-prone and obese-prone panel of dogs that were fed slightly below maintenance requirements (requirement=(1.3)(BW$_{0.75}$)(70)). Both groups were fed the control food for 1 week before testing started, and then randomly assigned to either the food containing coconut oil or the control food for 3 weeks. Both lean and obese dogs fed coconut oil lost significantly more weight than the control fed dogs (see FIG. 2). The lean group was taken off study at 2 weeks to avoid excessive body weight loss. All dogs consumed the allotted amount of food each day.

C. Study 3

Study 3 consisted of three groups of dogs fed rations in the following manner:

Group 1: Hill's prescription weight loss food r/d as a control.

Group 2: The same base food without fiber and containing 14.2% coconut oil.

Group 3: The same base food without fiber and containing 7.1% coconut oil.

Figure 3:
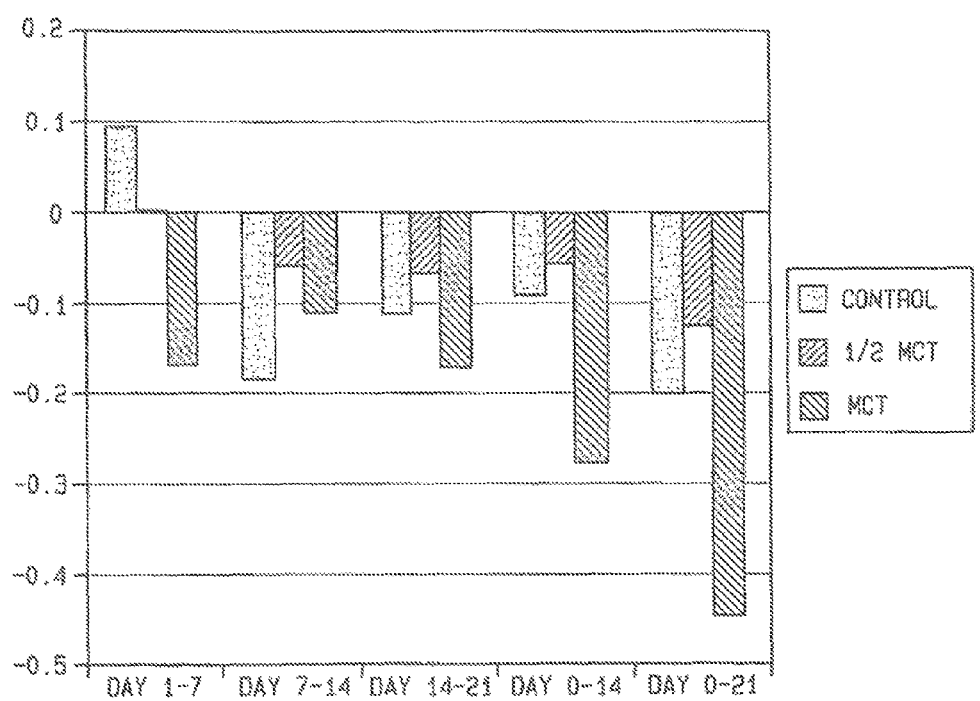
FIG. 3 compares observed body weight changes in dogs fed rations supplemented with MCT, rations supplemented with half the amount of MCT, and rations not supplemented with MCT.

All dogs were fed at their maintenance requirements (requirement=(1.6)(BW$^{0.75}$)(70)), and consumed all of their allotted food. The dogs of Group 2 lost significantly more body weight than dogs of Groups 1 and 3 (see FIG. 3).

D. Study 4

Study 4 consisted of four groups of obese dogs fed a food containing 0% or 13% coconut oil, and 1.4% or 21% fiber. The dogs were fed slightly below the maintenance requirements of their ideal body weight (requirement=(1.3)(ideal BW$^{0.75}$)(70)). As shown in Table 4 below, dogs fed the foods containing the 13% coconut oil lost at a greater rate than the dogs fed the control foods not containing the coconut oil.

TABLE 4

Rate of Body Weight Loss (grams/day)

| Formulation | Mean Rate of Loss | SEM |
|---|---|---|
| 1.4% fiber, 0% coconut oil | 28.0 | 3.9 |
| 1.4% fiber, 13% coconut oil | 39.6 | 3.9 |
| 21% fiber, 0% coconut oil | 37.7 | 3.9 |
| 21% fiber, 13% coconut oil | 43.8 | 3.9 |

E. Study 5

Study 5 consisted of food intake trials that tested foods containing MCT (i.e., 13% coconut oil) against commercially available dog foods used for weight loss or weight maintenance. In all cases, the dogs consumed more of the food containing MCT than the commercially available food (see Tables 5, 6, and 7).

TABLE 5

Food Intake (grams/day)

| Food | Intake (grams) |
|---|---|
| Food containing 13% coconut oil | 303 |
| Commercially available canine light food | 59 |

TABLE 6

Food Intake (grams/day)

| Food | Intake (grams) |
|---|---|
| Food containing 13% coconut oil | 310 |
| Commercially available canine senior food | 80 |

TABLE 7

Food Intake (grams/day)

| Food | Intake (grams) |
|---|---|
| Food containing 13% coconut oil | 211 |
| Commercially available canine maintenance food | 132 |

Example 2

In this experiment, the efficacy of a dietary addition of a high level of fiber (current Hill's Prescription Diet® Canine r/d® dry) to control appetite and enhance weight loss in obese dogs was compared with that of two prototype dry foods. Each prototype food had high levels of fat (coconut oil, a natural source of MCT), adequate protein, and moderate levels of carbohydrate (nitrogen-free extract or "NFE"). The prototypes differed in the levels of fiber.

The study was conducted over 16 weeks. The average initial body fat for the animals was 39.8%. The treatment and control groups are summarized in Table 8.

TABLE 8

Treatment and Control Groups

| Diet Description | No. of Animals |
|---|---|
| Prescription Diet ® Canine r/d ®, Dry (Positive Control) | 8 |
| Prototype 1 (with added MCT) | 8 |
| Prototype 2 (with added MCT and fiber) | 8 |

As indicated in Table 8, three foods were used in this experiment. The first food was Prescription Diet® Canine r/d® dry. This food was used as a positive control for weight loss. This is a weight-loss food that provides adequate nutrient intake and restriction of caloric intake for dogs. The second and third foods were prototypes with added MCT oil and without or with added fiber, respectively. These two foods maintained the same calorie-to-protein ratio as found in the positive control. The two foods are similar in nutrient composition in that they are high protein, high fat, and moderate carbohydrate. The compositions of these diets are shown in Table 9.

TABLE 9

Food Analysis

| | Canine r/d Dry | Prototype 1 | Prototype 2 (added fiber) |
|---|---|---|---|
| Protein % | 25.41 | 37.54 | 36.19 |
| Fat % | 10.24 | 21.48 | 21.35 |
| Crude fiber % | 22.88 | 2.05 | 5.87 |
| Ash % | 4.92 | 5.17 | 5.31 |
| NFE % | 35.55 | 33.76 | 31.28 |
| Calcium % | 0.71 | 0.92 | 0.93 |
| Phosphorus % | 0.58 | 0.78 | 0.81 |
| Potassium % | 0.80 | 0.64 | 0.65 |
| Sodium % | 0.28 | 0.44 | 0.43 |
| Magnesium % | 0.14 | 0.11 | 0.12 |
| Metabolizable energy, kcal/kg (calc'd using Atwater eq.) | 2942 | 4356 | 4193 |
| Calorie:Protein Ratio | 118.9 | 119.0 | 119.0 |

Composition percentages are based on a 100% dry weight of the composition.

The dogs were fed once daily, and typically consumed all the offered food. Daily consumption and food rejection were recorded. Food intake was restricted for the duration of the experiment to cause weight loss. Each dog received its daily food amount based on energy requirements of its ideal body weight. The formula used to determine the amount of calories offered to each animal was as follows: kcal offered per day=1.6×(70×ideal body weight (kg)$^{0.75}$). The amount of food offered daily to each animal was calculated by dividing the amount of calories to be offered by the caloric density of the food (kcal/kg). Use of this equation allowed animals to lose body weight at a rate of 1.0 to 1.5% of their initial body weight per week (the dogs lost weight at a rate of 1.00, 1.06, and 1.10 of their initial body weight per week for positive control, prototype 1, and prototype 2, respectively). Ideal body weight was estimated by calculating fat-free body mass from the Dual Energy X-Ray Absorptiometry (DEXA) analysis, and adding 20% fat to this total.

On Day 0, each dog was weighed, and body composition was determined via DEXA. Animals were allotted to treatments based on body composition, weight, and gender. On Day 1, each dog received a randomly assigned food, and then remained in its weight loss dietary treatment. The end of the study was determined for each dog by its meeting a body fat percentage of 20% or at the completion of 16 weeks on study. All dogs were weighed weekly, and scanned via DEXA every four weeks to measure their individual progress in weight loss.

Rates of weight change were derived from a regression equation relating weight change to time for each animal. The slope of each regression equation was used as the observation for each animal and these were combined within treatment to generate means for comparison.

Rates of fat tissue change were derived from a regression equation relating fat tissue change to time for each animal. The slope of each regression equation was used as the observation for each animal and these were combined within treatment to generate means for comparison.

Rates of lean tissue change were derived from a regression equation relating lean tissue change to time for each animal.

The results of this experiment are shown in Table 10.

TABLE 10

| Food | Rate of weight change, g/d | Rate of fat change, g/d | Rate of lean tissue change, g/d |
|---|---|---|---|
| Prescription diet r/d, dry | −20.4 | −17.4 | −3.1 |
| Prototype 1 | −24.0 | −20.4 | −2.3 |
| Prototype 2 | −23.2 | −15.0 | −5.5 |

As can be seen, the highest rate of weight change (−24.0 g/d) was in the dogs fed the prototype 1 food (without added fiber). This rate of change was not statistically different (P>0.05) than those fed Prescription Diet® Canine r/d® dry (−20.4 g/d) or the prototype 2 food with added fiber (−23.2 g/d). Thus, all foods tested in this study with the same calorie:protein ratio were effective for enhancing weight loss in obese dogs.

Most of the body weight change was related to change in body fat tissue. Dogs fed the prototype 1 food (without added fiber) had the highest rate of fat tissue change (−20.4 g/d). This rate of fat change was greater than those for the dogs fed Prescription Diet® Canine r/d® dry (−17.4 g/d) and the prototype 2 (food with added fiber) (−15.0 g/d).

All food treatments in this study resulted in loss of lean tissue. On average, the dogs lost from 0.26 to 0.62 kg of lean tissue over the duration of this study. Considering the dogs averaged 8.75 kg of lean tissue at the beginning of the study, this loss represents 3.0 to 7.1% of their total initial lean tissue. This small amount of lean tissue loss would not be deleterious to the health of the dogs.

Example 3

In this experiment, the efficacy of a dietary addition of a high level of fiber (current Hill's Prescription Diet® Feline r/d® dry) to control appetite and enhance weight loss in obese cats was compared with that of a prototype dry food. The prototype food had high level of fat (coconut oil, a natural source of MCT), adequate protein, and moderate levels of NFE.

This study was conducted over 24 weeks. The average initial body fat for the animals was 40.7%. The treatment and control groups are summarized in Table 11.

TABLE 11

Treatment and Control Groups

| Diet Description | No. of Animals |
|---|---|
| Prescription Diet ® Feline r/d ®, Dry (Positive Control) | 10 |
| Prototype 1 (with added MCT) | 10 |

As indicated in Table 11, two foods were used in this experiment. The first food was Prescription Diet® Feline r/d® dry. This food was used as a positive control for weight loss. This is a weight-loss food that provides adequate nutrient intake and restriction of caloric intake for cats. The second food was a prototype with added MCT oil.

The cats were fed once per day, and typically consumed all the offered food. Daily consumption and food rejection were recorded. Food intake was restricted for the duration of the experiment to cause weight loss. Each cat received its daily food amount based on energy requirements of its ideal body weight. The formula used to determine the amount of calories offered to each cat was as follows: kcal offered per day=0.8×(70×ideal body weight (kg)$^{0.75}$). The amount of food offered daily to each animal was calculated by dividing the amount of calories to be offered by the caloric density of the food (kcal/kg). Use of this equation allowed the animals to lose body weight at a rate of 0.5 to 1.0% of their initial body weight per week (the cats lost weight at a rate of −0.81 and −0.96% of their initial body weight per week for positive control and prototype 1, respectively). Ideal body weight was estimated by calculating fat-free body mass from the DEXA analysis and adding 20% fat to this total.

On day 0, each cat was weighed, and body composition was determined via DEXA. Animals were allotted to treatments based on body composition, weight, and gender. Beginning on day 1, each cat received a randomly assigned food, and then remained on its weight-loss dietary treatment. The end of the study was determined for each cat by its meeting a body fat percentage of 20% or at the completion of 24 weeks on study. All cats were weighed weekly, and scanned via DEXA every four weeks to measure their individual progress in weight loss.

The results of this experiment are shown in Table 12.

TABLE 12

| Food | Rate of weight change, g/d | % body weight change per week |
|---|---|---|
| Prescription Diet r/d, dry | −6.2 | −0.81 |
| Prototype 1 | −7.6 | −0.96 |

The highest rate of weight change (−7.6 g/d) was in the cats fed prototype 1 food (with the MCT oil added). This rate of change was not statistically different (P>0.05) than those fed Prescription Diet® Feline r/d® dry (−6.2 g/d). These results demonstrate that the foods tested in this study were effective for enhancing weight loss in obese cats.

\* \* \*

All the references cited above are incorporated by reference into this patent.

The words "comprise", "comprises", and "comprising" are to be interpreted inclusively rather than exclusively.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A solid food composition for animal consumption, wherein the composition comprises:
   (a) an active ingredient for use in aiding an animal in losing weight, wherein the active ingredient consists essentially of from about 12% to about 25% of one or more medium chain fatty acid triglycerides (based on dry weight of the composition); and
   (b) at least one of the following:
      (i) from about 5% to about 70% protein (based on dry weight of the composition); and
      (ii) from about 2% to about 50% fat (based on dry weight of the composition);
   (c) an agent to provide a benefit for weight management selected from the group consisting of nonfermentable fiber, chrominium-picolinate and mixtures thereof; and
   (d) from 0.0 to 5% (based on dry weight of the composition) of an additive selected from the group consisting of: iron oxide, sodium chloride, potassium citrate, potassium chloride, and mixtures thereof;
   with the proviso that the composition does not contain carnitine.

2. The composition according to claim 1, wherein the composition comprises at least one of the following:
   (a) no greater than about 50% carbohydrate (based on dry weight of the composition),
   (b) no greater than about 40% dietary fiber (based on dry weight of the composition), and
   (c) no greater than about 15% of one or more nutritional balancing agents (based on dry weight of the composition).

3. The composition according to claim 2, wherein the carbohydrate consists essentially of a nitrogen-free extract.

4. The composition according to claim 1, wherein the composition is a dry food.

5. The composition according to claim 1, wherein the composition is a wet food.

6. The composition according to claim 1, wherein at least a portion of one or more of the medium chain fatty acid triglycerides is from coconut oil.

7. The composition according to claim 1, wherein the composition comprises food manufactured for consumption by a cat, dog, bird, or farm animal.

8. A process for making a composition of claim 1, wherein the process comprises incorporating one or more medium chain fatty acid triglycerides into a companion animal food.

9. The process according to claim 8, wherein:
   the composition comprises kibbles; and
   the incorporation is accomplished by injecting at least about 2% of the one or more medium chain triglycerides into a preconditioner before kibble extrusion and coating any remaining amount of the one or more medium chain fatty acid triglycerides onto the kibbles after the extrusion.

10. A manufactured animal treat comprising the solid food composition of claim 1.

11. The treat according to claim 10, wherein the treat is manufactured for consumption by a cat or dog.

12. A manufactured toy comprising the solid food composition of claim 1.

13. The toy according to claim 12, wherein the toy comprises an artificial bone.

14. The toy according to claim 12, wherein the toy is manufactured for use by a cat or dog.

15. A process for making a toy of claim 12, wherein the process comprises coating an already existing toy with one or more medium chain fatty acid triglycerides.

\* \* \* \* \*